United States Patent [19]
Driessen-Hölscher et al.

[11] Patent Number: 5,834,611
[45] Date of Patent: Nov. 10, 1998

[54] COMPLEXES CONTAINING TRIS-(HYDROXYALKYL)-PHOSPHINES AS LIGANDS FOR TELOMERIZATIONS, AS CATALYSTS AND NEW COMPLEXES CONTAINING TRIS-(HYDROXYALKYL)-PHOSPHINES

[75] Inventors: Birgit Driessen-Hölscher; Wilhelm Keim; Thomas Prinz, all of Aachen; Hans-Joachim Traenckner, Bergisch Gladbach; Jörg-Dietrich Jentsch, Mülheim a.d.Ruhr, all of Germany

[73] Assignee: Bayer Aktiengesellschaft, Leverkusen, Germany

[21] Appl. No.: 878,589

[22] Filed: Jun. 19, 1997

[30] Foreign Application Priority Data

Jun. 27, 1996 [DE] Germany ................ 196 25 783.2

[51] Int. Cl.$^6$ .............. C07F 15/00; C07F 9/02; C07C 209/00; B01J 31/00
[52] U.S. Cl. ................. 556/21; 568/13; 568/15; 564/485; 502/162
[58] Field of Search ........ 568/13, 15; 564/485; 556/21; 502/162

[56] References Cited

U.S. PATENT DOCUMENTS

| | | | |
|---|---|---|---|
| 3,489,811 | 1/1970 | Drucker et al. | 260/606.5 |
| 3,970,532 | 7/1976 | Heckenbleikner et al. | 204/158 R |
| 4,142,060 | 2/1979 | Kuntz | 568/840 |
| 4,260,750 | 4/1981 | Kuntz | 544/178 |
| 4,356,333 | 10/1982 | Yoshimura et al. | 568/840 |
| 4,417,079 | 11/1983 | Yoshimura et al. | 568/903 |
| 5,206,396 | 4/1993 | Gruber et al. | 554/27 |

FOREIGN PATENT DOCUMENTS

| | | | |
|---|---|---|---|
| 0436226 | 7/1991 | European Pat. Off. | C07C 33/02 |
| 0773211 | 5/1997 | European Pat. Off. | C07C 209/60 |
| 1574239 | 7/1969 | France . | |
| 1553002 | 9/1979 | France | C07C 29/02 |
| 2693188 | 1/1994 | France | C07C 41/06 |
| 2601520 | 7/1976 | Germany | C07F 9/50 |
| 2733516 | 2/1978 | Germany | C07B 29/00 |
| 9630056 | 10/1996 | WIPO | A61K 51/10 |

OTHER PUBLICATIONS

J. Čermák, et al., Nickel(O) and Palladium(O) complexes With 1,3,5–Triaza–7–Phosphaadamantane. Catalysis of Buta–1,3–Diene Oligomerization or Telomerization in an Aqueous Biphasic System, Collect. Czech. Chem. Commun., vol. 62, pp. 355–363, (1997).

W.A. Herrmann, et al., Water–Soluble Ligands, Metal Complexes, and Catalysts: Synergism of Homogeneous and Heterogeneous Catalysis, Angew. Chem. Int. Ed. Engl., 32, pp. 1524–1544, (1993).

I.T. Horváth, et al., Aqueous Organometallic Chemistry and Catalysis, Kluwer Academic Publishers, pp. 112–122, (1995).

P.A.T. Hoye, et al., Hydrophosphination of Formaldehyde catalysed by Tris–(hydroxymethyl)phosphine Complexes of Platinum, Palladium or Nickel, Chem. Soc. Dalton Trans., pp. 269–274, (1993).

M.B. Smith, University of Bristol, Chapter 3 Synthesis, Characterisation and Catalytic Properties of Nickel(O), Palladium(O) and Platinum(O) Complexes of Tris(Hydroxymethyl)Phosphine, pp. 77–83, (1991).

P. Kalck, et al., Use of Water–Soluble Ligands in Homogeneous Catalysis, Advances in Organometallic Chemistry, vol. 34, pp. 219–282, (1992).

E. Monflier, et al., Palladium catalyzed telomerization of butadiene with water in a two phase system: drastic effect of the amine structure on the rate and selectivity, Journal of Molecular Catalysis A: Chemical, 97, pp. 29–33, (1995).

G. Peiffer, et al., Synthesis of Water–Soluble Ligands With a Quaternary Ammonium Salt: Use in Biphasic Palladium–Catalyzed Telomerisation of Butadiene and Isoprene, Journal of Molecular Catal., 59, pp. 1–9, (1990).

Birgit Driessen–Hölscher, et al., U.S. Application No. 8/740, 742, filed (Nov. 4, 1996).

Patent Abstracts of Japan, Abstract of JP 92 149 437, (Sep. 6, 1992).

Patent Abstracts of Japan, Abstract of JP 92 49 538, (Jun. 3, 1992).

*Primary Examiner*—Gary Geist
*Assistant Examiner*—Brian J. Davis
*Attorney, Agent, or Firm*—Sprung Kramer Schaefer & Briscoe

[57] ABSTRACT

In a process for the telomerization of dienes with nucleophiles in a liquid two-phase system, use is made as catalysts of complexes comprising a transition metal as central atom and at least one tris-(hydroxyalkyl)-phosphine or -phosphine oxide as ligand. The use as catalysts of compounds comprising a transition metal as central atom and at least one tris-(hydroxy-$C_2$–$C_5$-alkyl)-phosphine or -phosphine oxide as ligand, new compounds of this type and aqueous solutions of such compounds are likewise described.

2 Claims, No Drawings

COMPLEXES CONTAINING TRIS-(HYDROXYALKYL)-PHOSPHINES AS LIGANDS FOR TELOMERIZATIONS, AS CATALYSTS AND NEW COMPLEXES CONTAINING TRIS-(HYDROXYALKYL)-PHOSPHINES

The present invention relates to a telomerization process in which use is made as catalysts of complexes containing tris-(hydroxyalkyl)-phosphines as ligands, the general use of such complexes as catalysts and new complexes containing tris-(hydroxyalkyl)-phosphines as ligands.

DE-OS (German Published Specification) 2 601 520 describes the preparation of tris-(hydroxyethyl)-phosphine from vinyl acetate and phosphine in the presence of a free-radical initiator and acid hydrolysis. Other tris-(hydroxyalkyl)-phosphines can be obtained by an analogous method if other alkenyl acetates are used in place of vinyl acetate, e.g. propenyl, butenyl or pentenyl acetate. Tris-(hydroxyalkyl)-phosphines can, according to this publication, be used as starting material for preparing flame retardants and as monomers for preparing polyurethane ureas.

FR Patent 1 574 239 describes a similar synthesis of tris-(hydroxyalkyl)-phosphines, but using alkenols in place of alkenyl acetates. The use indicated for these phosphines is their addition to permanent wave compositions.

U.S. Pat. No. 3,489,811 describes the preparation of essentially odourless tris-(hydroxy-3-propyl)-phosphine from phosphine by reaction with allyl alcohol and the use of this phosphine for cosmetic purposes.

In general, various synthetic possibilities and uses are known for hydroxyalkyl-phosphines.

The liquid/liquid two-phase technique is a method for combining the advantages of homogeneous and heterogeneous catalysts. This method allows transition metal-containing catalysts to be separated from the products and any remaining starting materials by simple phase separation and then allows the catalyst phase to be reused directly for the next reaction (see Angew. Chem. 105, 1588 (1993), Adv. Organomet. Chem. 34, 219 (1992)). Telomerization reactions have already been carried out in two-phase systems.

DE-OS (German Published Specification) 2 733 516 discloses the telomerization of dienes with nucleophiles in a two-phase system. In this process, water was used as solvent for the catalyst and the catalyst was made water-soluble by complexing transition metal compounds with sulfonated phosphines. Nucleophiles used were water, alcohols, phenols, acids, amines, CH-active substances and silanols.

U.S. Pat. Nos. 4,356,333 and 4,417,079 and EP-A 436 226 describe a two-phase system for the telomerization of butadiene with water to give octadienol. The reaction is carried out in a water/sulfolane mixture from which the octadienols formed precipitate. The palladium catalyst is retained in the sulfolane phase by means of monosulfonated triphenylphosphine (TPPMS).

Water-soluble quaternary ammonium phosphines as ligands for transition metal catalysts have also been described in a two-phase system for the telomerization of dienes with methanol (J. Mol. Catal. 59, 1 (1990)).

FR Patent 2 693 188 describes the telomerization of sucrose with butadiene in aqueous solution using a catalyst system comprising palladium acetate and trisulfonated triphenylphosphine (TPPTS). The conversion based on sucrose is 96%. Various octadienyl ethers having different degrees of alkylation are formed, with the di-, tri- and tetraethers predominating.

The telomerization of butadiene and water in a two-phase system using a trialkylamine as additive has recently been described (J. Mol. Catal. A: Chemical 97, 29 (1995)). The catalyst system here comprises a palladium salt and TPPMS or TPPTS. The product mixture comprises up to 5-telomerization products from the group consisting of alcohols, olefins and ethers.

In summary, telomerizations using water-soluble, phosphine-containing complexes as catalysts have, up until now, only been carried out using phosphines containing strongly polar groups such as sulfonate or ammonium groups as ligands for such complexes. The known telomerizations using such catalysts frequently proceed unselectively, i.e. they give nonuniform product mixtures.

The thesis of M. B. Smith, University of Bristol (1991), discloses tris-(hydroxymethyl)-phosphine as ligand for complexes and the catalytic properties of such complexes.

According to the article by P. G. Pringle in I. T. Horvath and F. Joo, Aqueous Organometallic Chemistry and Catalysis, Kluwer Academic Press, p. 114 (1995), tris-(hydroxy-3-propyl)-phosphine was used as ligand for platinum complexes and was physically and chemically characterized. Nothing is said about catalytic effects of such complexes.

JP 92-149 437 and JP 92 49 538 describe catalysts for hydroformylations comprising rhodium and/or cobalt carbonyls and tris-(hydroxymethyl)-phosphine on a support.

As regards complexes having tris-(hydroxyalkyl)-phosphines as ligands, only two such complexes are known and catalytic properties are known for only one of these.

The present invention provides, firstly, a process for the telomerization of dienes with nucleophiles in a liquid two-phase system, wherein use is made as catalysts of complexes comprising a transition metal as central atom and at least one tris-(hydroxyalkyl)-phosphine or -phosphine oxide as ligand.

Suitable dienes are, for example, those which contain from 4 to 12 carbon atoms and may, if desired, be substituted by from 1 to 4 $C_1$–$C_4$-alkyl groups. Preferred dienes are conjugated dienes such as isoprene, 1,3-butadiene, 1,3-pentadiene, 2,3-dimethyl-1,3-butadiene, 2,4-hexadiene and myrcene.

A particularly preferred diene is 1,3-butadiene.

Suitable nucleophiles are, for example, water, alcohols, phenols, acids, ammonia, amines, imines, carbon dioxide, CH-active organic compounds and silanols.

Alcohols can contain, for example, from 1 to 12 carbon atoms, phenols can contain, for example, from 6 to 20 carbon atoms. Acids can be, for example, organic acids having from 1 to 10 carbon atoms which can be saturated or unsaturated and straight-chain, branched or cyclic and can contain, for example, from 1 to 3 carboxyl groups. Amines can contain, for example, from 1 to 30 carbon atoms and be primary or secondary. Imines can be, for example, straight-chain and contain from 1 to 10 carbon atoms or be cyclic and contain from 2 to 5 carbon atoms. The CH-active organic compounds can be, for example, methylene-carbonyl compounds such as benzyl methyl ketone, nitroalkanes such as nitroethane, nitriles such as ethyl cyanoacetate and sulfones such as ethyl (phenylsulfonyl)-acetate. Silanols can contain, for example, only silicon, oxygen and hydrogen atoms, but may also contain additional organic radicals each having, for example, from 1 to 10 carbon atoms.

Preferred nucleophiles are water and ammonia, with particular preference being given to ammonia.

From 0.1 to 10 mol of a nucleophile can, for example, be used per mol of the respective diene. This amount is preferably from 0.25 to 0.5 mol.

Suitable liquid two-phase systems are, for example, those in which one phase comprises water or a polar solvent and the other phase comprises a solvent which is immiscible or only sparingly miscible with the first phase. The liquid two-phase system can also comprise a hydrophilic phase and an organic phase which is immiscible or only sparingly miscible with water. The main constituent of the organic phase can be an organic solvent which is immiscible or only sparingly miscible with water. Suitable organic solvents are, for example, aliphatic and aromatic hydrocarbons, chlorinated aliphatic and aromatic hydrocarbons, ethers, tertiary amines and pyrrolidone. Preferred solvents are, for example, benzene, toluene and methylene chloride. It is also possible to use mixtures of organic solvents which are immiscible or only sparingly miscible with water. The respective diene used is also a possibility as the organic phase which is immiscible or only sparingly miscible with water.

The hydrophilic phase can, for example, be water or a hydrophilic organic solvent. Examples of hydrophilic organic solvents are $C_1$–$C_6$-alcohols and tetramethylene sulfone. The hydrophilic phase used is preferably water. It is also possible to use mixtures, e.g. mixtures of water with $C_1$–$C_6$-alcohols or with tetramethylene sulfone.

Preferred catalysts are those corresponding to the formula (I)

where $L^1$ represents a tris-(hydroxy-$C_1$–$C_5$-alkyl)-phosphine or -phosphine oxide ligand, $L^2$ represents a ligand selected from the group consisting of H, CO, NO, $PF_3$, $H_2O$, S, halogens, aromatic ligands, olefinic ligands and acetylenic ligands, M represents a metal or metal ion of a transition element of group I, VII or VIII of the Periodic Table of the Elements, x represents an integer from 1 to 6 and y represents zero or an integer from 1 to 5, where the sum of x and y is at most 6 and m represents 1, 2 or 3 and n, p and q each represent zero, 1, 2 or 3, where:

$$m \cdot p = n \cdot q \text{ and}$$

A represents an anion having the charge q.

$L^1$ preferably represents a tris-(hydroxy-$C_2$–$C_5$-alkyl)-phosphine or -phosphine oxide, particularly preferably tris-(hydroxypropyl)-phosphine or -phosphine oxide.

$L^2$ preferably represents H, CO, NO, Cl, allyl, methallyl, cyclopentadiene, cyclooctadiene, dibenzylideneacetone or diphenyl acetylene.

M preferably represents Mn, Fe, Co, Ni, Ru, Rh, Pd, Os, Ir or Pt or an ion of these metals, in particular nickel, palladium or platinum or an ion of these metals. M particularly preferably represents palladium or $Pd^{2+}$.

x preferably represents an integer from 2 to 4 and y preferably represents zero, 1 or 2, where the sum of x+y is preferably at most 4.

M can occur in all oxidation states usual for the respective metal. Preference is given to the oxidation states zero and +2. If M is present in a positive oxidation state, the $L_x^1 L_y^2 M$ part of the compound of the formula (I) is a correspondingly positively charged complex ion. The charge of such complex ions can be compensated by any anions A, for example by halide, carboxylate, 1,3-diketonate, nitrate, phosphate, sulfate and/or tetrafluoroborate ions. Preferred anions A are chloride, acetate, acetylacetonate and nitrate ions.

If $L^1$ is a tris-(hydroxyalkyl)-phosphine or -phosphine oxide in which the alkyl group contains 2 or more carbon atoms, the hydroxy group on the alkyl group can be bound to any carbon atom. The hydroxy group is preferably bound to the terminal carbon atom of the alkyl group, i.e. as far as possible from the central phosphorus atom.

Particularly preferred individual complexes of the formula (I) are bis-[tris-(hydroxy-3-propyl)-phosphine] palladium(II) acetate, tetrakis-[tris-(hydroxy-3-propyl)-phosphine]palladium(II) acetate, dibenzylideneacetone-tetrakis-[tris-(hydroxy-3-propyl)-phosphine]palladium(0), tris-[tris-(hydroxy-3-propyl)-phosphine]palladium(0), tetrakis-[tris-(hydroxy-3-propyl)-phosphine]palladium(0), the corresponding phosphine oxides and the corresponding compounds additionally containing dibenzylideneacetone ligands.

From 0.01 to 0.001 mol of catalyst can, for example, be used per 1 mol of diene. This amount is preferably from 0.002 to 0.005 mol.

The telomerization process of the invention can be carried out, for example, at temperatures in the range from 30° to 150° C. and pressures in the range from 1 to 30 bar. It is preferably carried out at from 50° to 120° C. in an autoclave, under the autogenous pressure at the reaction temperature.

The reaction is generally complete after from 1 to 20 hours. It is advantageous to stir or to shake the reaction vessel during the reaction. The reaction mixture obtained after the reaction can be worked up in a simple manner. For example, the procedure can be to separate the aqueous phase from the organic phase, to wash the aqueous phase with an organic solvent which is immiscible or only sparingly miscible with water, preferably the organic solvent used in the reaction, to combine the washing liquid with the separated organic phase and to separate off and fractionate the telomerization products obtained, e.g. by distillation or crystallization.

In a preferred embodiment of the telomerization process of the invention, the catalyst and water are placed in an autoclave at room temperature, the nucleophile, the organic solvent which is immiscible or only sparingly miscible with water and a measured amount of diene are added at low temperature and the autoclave is, after being closed, heated to the reaction temperature. After the reaction is complete and any further stirring, the autoclave is finally brought to room temperature, it is vented and the reaction mixture obtained is worked up, for example as described above.

The telomerization process of the invention can be carried out batchwise or continuously. It is particularly suitable for preparing octadienylamines from butadiene and ammonia and for preparing octadienols from butadiene and water.

The complexes to be used according to the invention can be prepared in a simple manner. For example, it is possible to initially charge a salt or a known complex of a transition metal and water and to add to this mixture at least the amount of a tris-(hydroxyalkyl)-phosphine or -phosphine oxide theoretically required to form the respective complex to be used according to the invention. Ligands other than tris-(hydroxyalkyl)-phosphines and -phosphine oxides, for example those which are denoted by the symbol $L^2$ in formula (I), can, for example, be added together with the transition metal salt or the known transition metal complex or separately. The phosphine or phosphine oxide and any further ligands are preferably used in the stoichiometrically required amount. It is also possible to employ less than or more than the stoichiometrically required amounts of phosphines or phosphine oxides and any further ligands.

The amount of water can, for example, be such that from 10 to 100 ml of water are employed per 1 mmol of transition metal salt used or 1 mmol of transition metal complex used.

The above procedure gives an aqueous solution of a complex to be used according to the invention. This is largely free of any undesired impurities if stoichiometric amounts of the starting materials have been employed. It is frequently not necessary to isolate complexes to be used according to the invention from this aqueous solution. They can also be used in the telomerization process of the invention in the form of aqueous solutions, particularly in the form of those aqueous solutions as are obtained in the preparation described here.

The present invention further provides for the general use of complexes of the formula

where
L$^{1'}$ represents a tris-(hydroxy-C$_2$–C$_5$-alkyl)-phosphine or -phosphine oxide ligand,
and the other symbols used are as defined for formula (I) and are linked to one another in the manner indicated for formula (I), as catalysts. L$^{1'}$ preferably represents tris-(hydroxypropyl)-phosphine or -phosphine oxide. The other symbols used have the preferred and particularly preferred meanings given for formula (I).

Complexes of the formula (I') can be used not only for the telomerization of dienes with nucleophiles in liquid two-phase systems, but also, for example, for any telomerizations, for hydrogenations, for C—C linkages and, in combination with noble metal carbonyls, for hydroformylations.

The present invention further provides new compounds of the formula

where p1 L$^{1''}$ represents a tris-(hydroxy-C$_2$–C$_5$-alkyl)-phosphine or -phosphine oxide ligand with the exception of tris-(hydroxy-3-propyl)-phosphine
and the other symbols used are as defined for formula (I) and are linked to one another in the manner indicated for formula (I). L$^{1''}$ is preferably tris-(hydroxyethyl, hydroxy-2-propyl, hydroxy-4-butyl or hydroxy-5-pentyl)-phosphine or -phosphine oxide. The other symbols used have the preferred and particularly preferred meanings given for formula (I).

A method of preparation for catalysts of the formula (I) in which the catalysts are obtained in the form of an aqueous solution has been described above, and it has been indicated that these catalysts can also be used in the form of aqueous solutions in the telomerization process of the invention.

The present invention therefore also provides aqueous solutions of complexes, wherein the dissolved complexes comprise a transition metal as central atom and at least one tris-(hydroxy-C$_2$–C$_5$-alkyl)-phosphine or -phosphine oxide as ligand, and provides for the use of such aqueous solutions of complexes as catalysts in liquid two-phase systems.

Aqueous solutions according to the invention preferably and particularly preferably comprise complexes which correspond to the formula (I') and preferably and particularly preferably comprise complexes of the formula (I') which are described there as preferred and particularly preferred. Aqueous solutions according to the invention are generally colorless to yellow/red in color.

Liquid two-phase systems in which aqueous solutions of complexes according to the invention can be used as catalyst generally comprise an aqueous phase and a phase comprising an organic solvent which is immiscible or only sparingly miscible with water.

The compounds of the formulae (I), (I') and (I") can, if desired, be isolated in a simple manner from the aqueous solution obtained in the above-described preparation of catalysts of the formula (I), for example by taking off the water and working up the remaining residue by chromatography.

The telomerization process of the invention and thus also the use of complexes of the formula (I') and the new compounds of the formula (I") allow the preparation of octadienylamines from butadiene and ammonia in good yields and with good selectivities. After the reaction, the catalyst is present in one phase and the reaction products are present in the other phase. This makes a simple work-up possible and leads to minimal catalyst losses or no catalyst losses at all.

It is extremely surprising that these advantages occur, since it could not have been expected on the basis of the prior art that phosphines and phosphine oxides having hydroxy groups, which are less polar than sulfonate or ammonium groups, give the transition metal complexes a sufficiently good water solubility and a sufficiently low solubility in organic media. Rather, it would have been expected that the complexes of the invention would not dissolve sufficiently in water and therefore would not be usable as catalysts for liquid two-phase systems.

EXAMPLES

General procedure for preparing the transition metal complexes containing tris-(hydroxyalkyl)-phosphines or -phosphine oxides as ligand.

From 1 to 6 equivalents of tris-(hydroxyalkyl)-phosphine or -phosphine oxide dissolved in water were added to one equivalent of metal salt or metal complex. The mixture was stirred for a few minutes at room temperature. The metal compound which was originally usually not soluble went into solution during this time. This gave colorless to yellow-red-colored homogeneous solutions which were used in this form for catalysing telomerization reactions in liquid two-phase systems.

Example 1

A catalyst solution prepared from 0.15 mmol of palladium (II) acetate and 0.3 mmol of tris(3-hydroxypropyl)phosphine in 5 ml of water was placed in an autoclave filled with inert gas and 20 ml of a 27.13 molar aqueous ammonia solution and 12.5 ml of toluene were added. The autoclave was weighed and then cooled in an ethanol/dry ice mixture. 5.8 ml of liquid butadiene were then added and the autoclave was brought back to room temperature over a period of 1 hour. It was weighed again to accurately determine the amount of butadiene added and was then hung in an oil bath preheated to 80° C. After a reaction time of 17 hours, the autoclave was cooled to room temperature, then vented and opened. The contents were transferred to a separating funnel and the phases were separated. The aqueous phase was extracted with 10 ml of toluene. To remove remaining butadiene, argon was blown through the combined organic phases. A sample was subsequently taken from the combined organic phases, and this was dried over a molecular sieve and analyzed by gas chromatography.

Results of the gas-chromatographic analysis

The reaction mixture analyzed contained essentially octa-2,7-dienyl-1-amine (1) and octa-1,7-dienyl-3-amine (2) as reaction products.

Selectivity to (1): 66% Conversion to (1): 45%

Selectivity to (2): 18% Conversion to (2): 12%

In addition, secondary amines had been formed with a selectivity of 9%.

The total conversion to telomerization products was 63%.

Example 2

The procedure of Example 1 was repeated, but using 0.6 mmol of tris(3-hydroxypropyl)phosphine
Results of the gas-chromatographic analysis Selectivity to (1): 54% Conversion to (1) 34%

Selectivity to (2): 29% Conversion to (2) 18%

In addition, secondary amines had been formed with a selectivity of 9%.

The total conversion to telomerization products was 58%.

Example 3

The procedure of Example 2 was repeated, but 0.15 mmol of bis-(dibenzylideneacetone)-palladium was used in place of 0.15 mmol of palladium(II) acetate and the reaction was ended after 14.5 hours.
Results of the gas-chromatographic analysis Selectivity to (1): 50% Conversion to (1): 25%

Selectivity to (2): 28% Conversion to (2): 14%

In addition, secondary amines had been formed with a selectivity of 4.5%.

The total conversion to telomerization products was 41.5%.

Example 4

The procedure of Example 3 was repeated, but 0.6 mmol of tris(3-hydroxypropyl)phosphine oxide were used as phosphine.
Results of the gas-chromatographic analysis Selectivity to (1): 55% Conversion to (1): 2.7%

Selectivity to (2): 1% Conversion to (2): 0.3%

In addition, secondary amines had been formed with a selectivity of 1%, which is very advantageous.

The total conversion to telomerization products was 4%.

Example 5

0.113 mmol of $Pd(OAc)_2$ and 0.339 mmol of tris(3-hydroxypropyl)phosphine were dissolved in 30 ml of a 27.15% strength by weight aqueous $NH_3$ solution and introduced into a 125 ml steel autoclave. 38 g of butadiene were subsequently condensed into this. While mixing intensively, the autoclave was then held for 4 hours at an internal temperature of 80° C. It was subsequently cooled to room temperature in an ice bath and the excess butadiene was removed from the autoclave via a needle valve. The contents were then admixed with 10 ml toluene and transferred to a separating funnel. The organic phase was separated off, the aqueous phase was extracted once more with 10 ml of toluene and the combined organic phases were dried over molecular sieves. A sample of this solution was taken and analysed by gas chromatography.
Results of the gas-chromatographic analysis The reaction mixture analysed contained essentially octa-2,7-dienyl-1-amine (1) and octa-1,7-dienyl-3-amine (2) as reaction products.

Selectivity to (1): 53% Conversion to (1): 0.4% based on butadiene

Selectivity to (2): 41% Conversion to (2): 0.32% based on butadiene

Total yield: 0.8% based on butadiene.

The conversions and yields based on butadiene are low because it was present in a large excess.

Example 6

31.0 mg of bis-($\mu^3$-allyl-$\mu$-iodopalladium) were dissolved in 5 ml of an aqueous 27.15% strength by weight $NH_3$ solution and added to 22 mg of silver tetrafluoroborate dissolved in 5 ml of 27.15% strength by weight $NH_3$ solution. The precipitated silver iodide is filtered off with the aid of Celite® and rinsed with a total of 10 ml of an aqueous 27.15% strength by weight $NH_3$ solution. This colorless solution was transferred to a 125 ml steel autoclave and 38 g of butadiene were subsequently condensed in. While stirring vigorously, the autoclave was heated to 80° C. and a solution of 47 mg of tris(3-hydroxypropyl)phosphine in 10 ml of an aqueous 27.15% strength by weight $NH_3$ solution was then added via a dropping funnel. The autoclave was held at 80° C. for a further 0.75 hours while mixing vigorously. It was subsequently cooled to room temperature in an ice bath. The further work-up was carried out using a method similar to Example 5.
Results of the gas-chromatographic analysis The reaction mixture analyzed contained essentially octa-2,7-dienyl-1-amine (1) and octa-1,7-dienyl-3-amine (2) as reaction products.

Selectivity to (1): 47% Conversion to (1): 0.06% based on butadiene

Selectivity to (2): 40% Conversion to (2): 0.05% based on butadiene

Total yield: 0.12% based on butadiene.

The conversions and yields based on butadiene are low because it was present in a large excess.

Example 7

The procedure of Example 6 was repeated, but using 23.5 mg of tris(3-hydroxypropyl)phosphine and a reaction time of 4 hours.
Results of the gas-chromatographic analysis The reaction mixture analyzed contained essentially octa-2,7-dienyl-1-amine (1) and octa-1,7-dienyl-3-amine (2) as reaction products.

Selectivity to (1): 85% Conversion to (1): 1.53% based on butadiene

Selectivity to (2): 9% Conversion to (2): 0.16% based on butadiene

Total yield: 1.8% based on butadiene.

The conversions and yields based on butadiene are low because it was present in a large excess.

Example 8

The procedure of Example 6 was repeated, but the reaction time was 15 hours.
Results of the gas-chromatographic analysis The reaction mixture analyzed contained essentially octa-2,7-dienyl-1-amine (1) and octa-1,7-dienyl-3-amine (2) as reaction products.

Selectivity to (1): 54% Conversion to (1): 2.7% based on butadiene

Selectivity to (2): 28% Conversion to (2): 1.4% based on butadiene

Total yield: 5% based on butadiene.

The conversions and yields based on butadiene are low because it was present in a large excess.

Example 9

The procedure of Example 6 was repeated, but using 23.5 mg of tris(3-hydroxypropyl)phosphine and a reaction time of 15 hours.

Results of the gas-chromatographic analysis

The reaction mixture analyzed contained essentially octa-2,7-dienyl-1-amine (1) and octa-1,7-dienyl-3-amine (2) as reaction products.

Selectivity to (1): 68% Conversion to (1): 6.8% based on butadiene

Selectivity to (2): 11% Conversion to (2): 1.1% based on butadiene

Total yield: 10% based on butadiene.

What is claimed is:

1. A process for the telomerization of dienes which contain from 4 to 12 carbon atoms and which may, if desired, be substituted by from 1 to 4 $C_1$–$C_4$-alkyl groups, with nucleophiles selected from the group consisting of water, alcohols, phenols, acids, ammonia, amines, imines, carbon dioxide, CH-active organic compounds and silanols, in a liquid two-phase system in, which one phase comprises water or a polar solvent and the other phase comprises a solvent which is immiscible or only sparingly miscible with the first phase, in the presence of a catalyst of the formula (I)

$$[L^1{}_x L^2{}_y M]_m^{p+} [A]_n^{q-} \qquad (I),$$

where $L^1$ represents a tris-(hydroxy-$C_1$–$C_5$-alkyl)-phosphine or -phosphine oxide ligand, $L^2$ represents a ligand selected from the group consisting of H, CO, NO, $PF_3$, $H_2O$, S, halogens, aromatic ligands, olefinic ligands and acetylenic ligands, M represents a metal or metal ion of a transition element of group I, VII or VIII of the Periodic Table of the Elements, x represents an integer from 1 to 6 and y represents zero or an integer from 1 to 5, where the sum of x and y is at most 6 and m represents 1, 2 or 3 and n, p and q each represent zero, 1, 2 or 3, where:

$$m \cdot p = n \cdot q \text{ and}$$

A represents an anion having the charge q.

2. The process as claimed in claim 1, wherein from 0.01 to 0.001 mol of catalyst is used per mol of diene and the reaction is carried out at from 30° to 150° C. and from 1 to 30 bar.

* * * * *